US012189453B2

(12) United States Patent
Arakawa

(10) Patent No.: US 12,189,453 B2
(45) Date of Patent: Jan. 7, 2025

(54) INFORMATION PROCESSING DEVICE, WEARABLE DEVICE, INFORMATION PROCESSING METHOD, AND STORAGE MEDIUM

(71) Applicant: NEC Corporation, Tokyo (JP)

(72) Inventor: Takayuki Arakawa, Tokyo (JP)

(73) Assignee: NEC CORPORATION, Tokyo (JP)

( * ) Notice: Subject to any disclaimer, the term of this patent is extended or adjusted under 35 U.S.C. 154(b) by 491 days.

(21) Appl. No.: 17/299,906

(22) PCT Filed: Dec. 19, 2018

(86) PCT No.: PCT/JP2018/046880
§ 371 (c)(1),
(2) Date: Jun. 4, 2021

(87) PCT Pub. No.: WO2020/129198
PCT Pub. Date: Jun. 25, 2020

(65) Prior Publication Data
US 2022/0026975 A1 Jan. 27, 2022

(51) Int. Cl.
G06F 1/3234 (2019.01)
A61B 5/117 (2016.01)
(Continued)

(52) U.S. Cl.
CPC ............ G06F 1/3234 (2013.01); A61B 5/117 (2013.01); G06F 21/32 (2013.01); H04R 1/1016 (2013.01);
(Continued)

(58) Field of Classification Search
CPC ....... G06F 1/3234; G06F 21/32; A61B 5/117; A61B 2562/0204; H04R 1/1016; H04R 1/1041; H04R 2420/07
See application file for complete search history.

(56) References Cited

U.S. PATENT DOCUMENTS 5,787,187 A * 7/1998 Bouchard ................ A61B 5/12
235/382
9,558,336 B2 * 1/2017 Lee .......................... A61B 5/349
(Continued)

FOREIGN PATENT DOCUMENTS

CN 108697380 A 10/2018
EP 4325383 A1 * 2/2024 ............. G06F 1/163
(Continued)

OTHER PUBLICATIONS

Extended European Search Report for EP Application No. EP18944027.4 dated on Nov. 24, 2021.
(Continued)

Primary Examiner — Aurel Prifti
(74) Attorney, Agent, or Firm — Sughrue Mion, PLLC

(57) ABSTRACT

Provided is an information processing device including a wearing determination unit configured to determine whether or not a user wears a wearable device that emits a sound wave to perform a biometric authentication based on acoustic characteristics toward a part of a head of the user and an operation mode controlling unit configured to switch, based on a result of a determination by the wearing determination unit, an operation mode of the wearable device between a plurality of operation modes including a first operation mode in which a process for the biometric authentication is not executable and a second operation mode in which a process for the biometric authentication is executable.

19 Claims, 11 Drawing Sheets

(51) Int. Cl.
*G06F 21/32* (2013.01)
*H04R 1/10* (2006.01)

(52) U.S. Cl.
CPC .... *H04R 1/1041* (2013.01); *A61B 2562/0204* (2013.01); *H04R 2420/07* (2013.01)

(56) References Cited

U.S. PATENT DOCUMENTS

| | | | | |
|---|---|---|---|---|
| 10,477,319 | B2* | 11/2019 | Lou | H04R 5/033 |
| 10,824,192 | B2* | 11/2020 | Guo | G06F 3/0346 |
| 10,896,682 | B1* | 1/2021 | Dusan | G10L 15/00 |
| 11,042,618 | B2* | 6/2021 | Lesso | G10K 11/17823 |
| 11,089,429 | B1* | 8/2021 | Trivedi | H04R 1/1041 |
| 11,159,868 | B2* | 10/2021 | Chun | H04R 1/1041 |
| 11,475,899 | B2* | 10/2022 | Lesso | G10L 17/10 |
| 11,487,861 | B2* | 11/2022 | Lesso | G10L 25/51 |
| 11,494,473 | B2* | 11/2022 | Mukund | H04L 9/3231 |
| 2008/0262382 | A1* | 10/2008 | Akkermans | G06V 40/10 |
| | | | | 600/559 |
| 2010/0235667 | A1* | 9/2010 | Mucignat | G06F 1/3203 |
| | | | | 713/323 |
| 2011/0235818 | A1* | 9/2011 | Cozens | H04R 1/1066 |
| | | | | 381/74 |
| 2014/0037101 | A1* | 2/2014 | Murata | H04R 1/1041 |
| | | | | 381/74 |
| 2014/0314247 | A1* | 10/2014 | Zhang | H04R 1/1041 |
| | | | | 381/74 |
| 2015/0112157 | A1 | 4/2015 | Bijjani et al. | |
| 2016/0189451 | A1* | 6/2016 | Yoo | H04W 12/06 |
| | | | | 340/5.82 |
| 2016/0241553 | A1* | 8/2016 | Kim | H04W 12/33 |
| 2017/0032168 | A1* | 2/2017 | Kim | H04L 63/0861 |
| 2017/0164120 | A1* | 6/2017 | Johansen | H04R 25/305 |
| 2017/0185103 | A1* | 6/2017 | Kim | G06V 10/17 |
| 2017/0347180 | A1* | 11/2017 | Petrank | G06F 3/165 |
| 2018/0014103 | A1* | 1/2018 | Martin | H04R 1/1025 |
| 2018/0070166 | A1* | 3/2018 | Howell | H04R 1/1016 |
| 2018/0113673 | A1* | 4/2018 | Sheynblat | G10L 17/00 |
| 2018/0132031 | A1* | 5/2018 | Seo | H04R 1/1016 |
| 2018/0220220 | A1* | 8/2018 | Eim | H04R 1/1016 |
| 2018/0307818 | A1* | 10/2018 | Yano | A61B 5/117 |
| 2019/0052951 | A1* | 2/2019 | Kofman | H04R 1/1041 |
| 2019/0110121 | A1* | 4/2019 | Sapozhnykov | H04R 1/1041 |
| 2019/0187950 | A1* | 6/2019 | Takemura | H04R 5/0335 |
| 2019/0189129 | A1 | 6/2019 | Arakawa et al. | |
| 2019/0215611 | A1* | 7/2019 | Lou | H04R 1/1041 |
| 2019/0238969 | A1 | 8/2019 | Koike et al. | |
| 2019/0246196 | A1* | 8/2019 | Han | G06F 3/0488 |
| 2019/0333522 | A1* | 10/2019 | Lesso | G10L 17/06 |
| 2019/0335000 | A1* | 10/2019 | Zhang | H04L 67/125 |
| 2019/0335266 | A1* | 10/2019 | Wurtz | H04R 29/001 |
| 2020/0103932 | A1* | 4/2020 | Sanghi | G06F 1/324 |
| 2020/0401735 | A1* | 12/2020 | Kurosawa | G06F 3/162 |
| 2022/0391487 | A1* | 12/2022 | Mahmood | H04L 63/0861 |

FOREIGN PATENT DOCUMENTS

| | | | | |
|---|---|---|---|---|
| GB | 2584496 | A * | 12/2020 | G06F 21/32 |
| JP | 2004-065363 | A | 3/2004 | |
| JP | 2004-258963 | A | 9/2004 | |
| JP | 2005-223629 | A | 8/2005 | |
| JP | 2006-352523 | A | 12/2006 | |
| JP | 2007-165940 | A | 6/2007 | |
| JP | 2009-207053 | A | 9/2009 | |
| JP | 2009-232423 | A | 10/2009 | |
| JP | 2013-506891 | A | 2/2013 | |
| JP | 2014-033303 | A | 2/2014 | |
| JP | 2017-038766 | A | 2/2017 | |
| JP | 2017-153067 | A | 8/2017 | |
| WO | 2017/069118 | A1 | 4/2017 | |
| WO | 2018/034178 | A1 | 2/2018 | |
| WO | 2018/079139 | A1 | 5/2018 | |

OTHER PUBLICATIONS

Japanese Office Action for JP Application No. 2022-022534, mailed on Jan. 19, 2023 with English Translation.
International Search Report for PCT Application No. PCT/JP2018/046880, mailed on Mar. 12, 2019.
CN Office Action for CN Application No. 201880100301.8, mailed on Dec. 5, 2023 with English Translation.

* cited by examiner

INFORMATION PROCESSING DEVICE, WEARABLE DEVICE, INFORMATION PROCESSING METHOD, AND STORAGE MEDIUM

This application is a National Stage Entry of PCT/JP2018/046880 filed on Dec. 19, 2018, the contents of all of which are incorporated herein by reference, in their entirety.

TECHNICAL FIELD

The example embodiments relate to an information processing device, a wearable device, an information processing method, and a storage medium.

BACKGROUND ART

Patent Literature 1 discloses an earphone for performing personal authentication based on acoustic characteristics of an ear canal of a user or the like.

CITATION LIST

Patent Literature

PTL 1: International Publication No. WO2018/034178

SUMMARY OF INVENTION

Technical Problem

Processing of biometric authentication using acoustic characteristics as shown in Patent Literature 1 requires a large amount of power. For this reason, in a wearable device that performs biometric authentication based on acoustic characteristics, reduction in power consumption may be required.

The example embodiments intend to provide an information processing device, a wearable device, an information processing method, and a storage medium which can reduce power consumption in a wearable device that performs biometric authentication based on acoustic characteristics.

Solution to Problem

According to one example aspect of the invention, provided is an information processing device including a wearing determination unit configured to determine whether or not a user wears a wearable device that emits a sound wave to perform a biometric authentication based on acoustic characteristics toward a part of a head of the user and an operation mode controlling unit configured to switch, based on a result of a determination by the wearing determination unit, an operation mode of the wearable device between a plurality of operation modes including a first operation mode in which a process for the biometric authentication is not executable and a second operation mode in which a process for the biometric authentication is executable.

According to another example aspect of the invention, provided is a wearable device emitting a sound wave to perform a biometric authentication based on acoustic characteristics toward a part of a head of a user including a wearing determination unit configured to determine whether or not the user wears the wearable device and an operation mode controlling unit configured to switch, based on a result of a determination by the wearing determination unit, an operation mode of the wearable device between a plurality of operation modes including a first operation mode in which a process for the biometric authentication is not executable and a second operation mode in which a process for the biometric authentication is executable.

According to another example aspect of the invention, provided is an information processing method including determining whether or not a user wears a wearable device that emits a sound wave to perform a biometric authentication based on acoustic characteristics toward a part of a head of the user and switching, based on a result of a determination, an operation mode of the wearable device between a plurality of operation modes including a first operation mode in which a process for the biometric authentication is not executable and a second operation mode in which a process for the biometric authentication is executable.

According to another example aspect of the invention, provided is a storage medium storing a program that causes a computer to perform determining whether or not a user wears a wearable device that emits a sound wave to perform a biometric authentication based on acoustic characteristics toward a part of a head of the user and switching, based on a result of a determination, an operation mode of the wearable device between a plurality of operation modes including a first operation mode in which a process for the biometric authentication is not executable and a second operation mode in which a process for the biometric authentication is executable.

Advantageous Effects of Invention

According to the example embodiments, an information processing device, a wearable device, an information processing method, and a storage medium which can reduce power consumption in a wearable device that performs biometric authentication based on acoustic characteristics.

DESCRIPTION OF EMBODIMENTS

Example embodiments will be described below with reference to the drawings. Throughout the drawings, the same components or corresponding components are labeled with same references, and the description thereof may be omitted or simplified.

First Example Embodiment

An information processing system according to the example embodiment will be described. The information processing system of the example embodiment is a system for performing wearing detection of a wearable device such as an earphone and biometric authentication.

Figure 1:
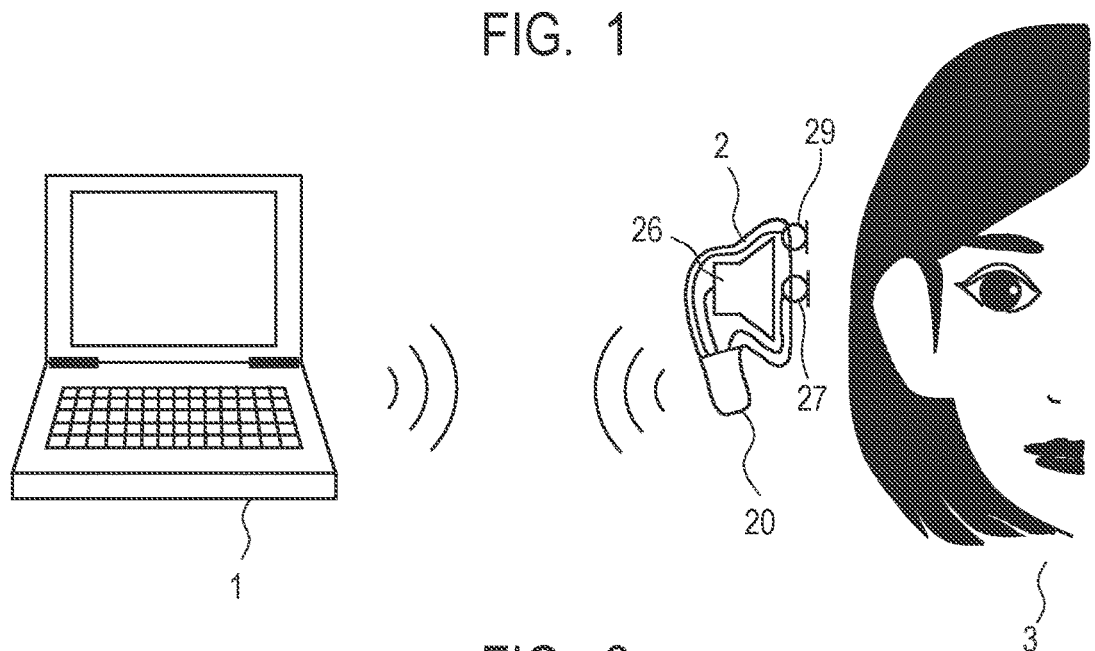
FIG. 1 is a schematic diagram illustrating a general configuration of an information processing system according to a first example embodiment.

FIG. 1 is a schematic diagram illustrating a general configuration of an information processing system according to the example embodiment. The information processing system is provided with an information communication device 1 and an earphone 2 which may be connected to each other by wireless communication.

The earphone 2 includes an earphone control device 20, a speaker 26, a microphone 27, and an infrared sensor 29. The earphone 2 is an acoustic device which can be worn on the ear of the user 3, and is typically a wireless device such as a wireless earphone, a wireless headset or the like. The speaker 26 functions as a sound wave generation unit which emits a sound wave toward the ear canal of the user 3 when worn, and is arranged on the wearing surface side of the earphone 2. The microphone 27 is also arranged on the wearing surface side of the earphone 2 so as to receive sound waves reflected by the ear canal or the like of the user 3 when worn. The infrared sensor 29 functions as a wearing detection unit for detecting infrared rays emitted from the user 3 when worn, and is composed of a photodiode or the like. The infrared sensor 29 is arranged on the wearing surface side of the earphone 2. The earphone control device 20 controls the speaker 26, the microphone 27, and the infrared sensor 29 and communicates with an information communication device 1.

Note that, in the specification, "sound" such as sound waves and voices includes inaudible sounds whose frequency or sound pressure level is outside the audible range.

The information communication device 1 is, for example, a computer that is communicatively connected to earphone 2, and controls the operation of the earphone 2, transmits audio data for generating sound waves emitted from the earphone 2, and receives audio data acquired from the sound waves received by the earphone 2. As a specific example, when the user 3 listens to music using the earphone 2, the information communication device 1 transmits compressed data of music to the earphone 2. When the earphone 2 is a telephone device for business command at an event site, a hospital or the like, the information communication device 1 transmits audio data of the business instruction to the earphone 2. In this case, the audio data of the utterance of the user 3 may be transmitted from the earphone 2 to the information communication device 1. The information communication device 1 or the earphone 2 may have a function of ear acoustic authentication using sound waves received by the earphone 2.

Note that, the general configuration is an example, and for example, the information communication device 1 and the earphone 2 may be connected by wire. Further, the information communication device 1 and the earphone 2 may be configured as an integrated device, and further another device may be included in the information processing system.

Figure 2:
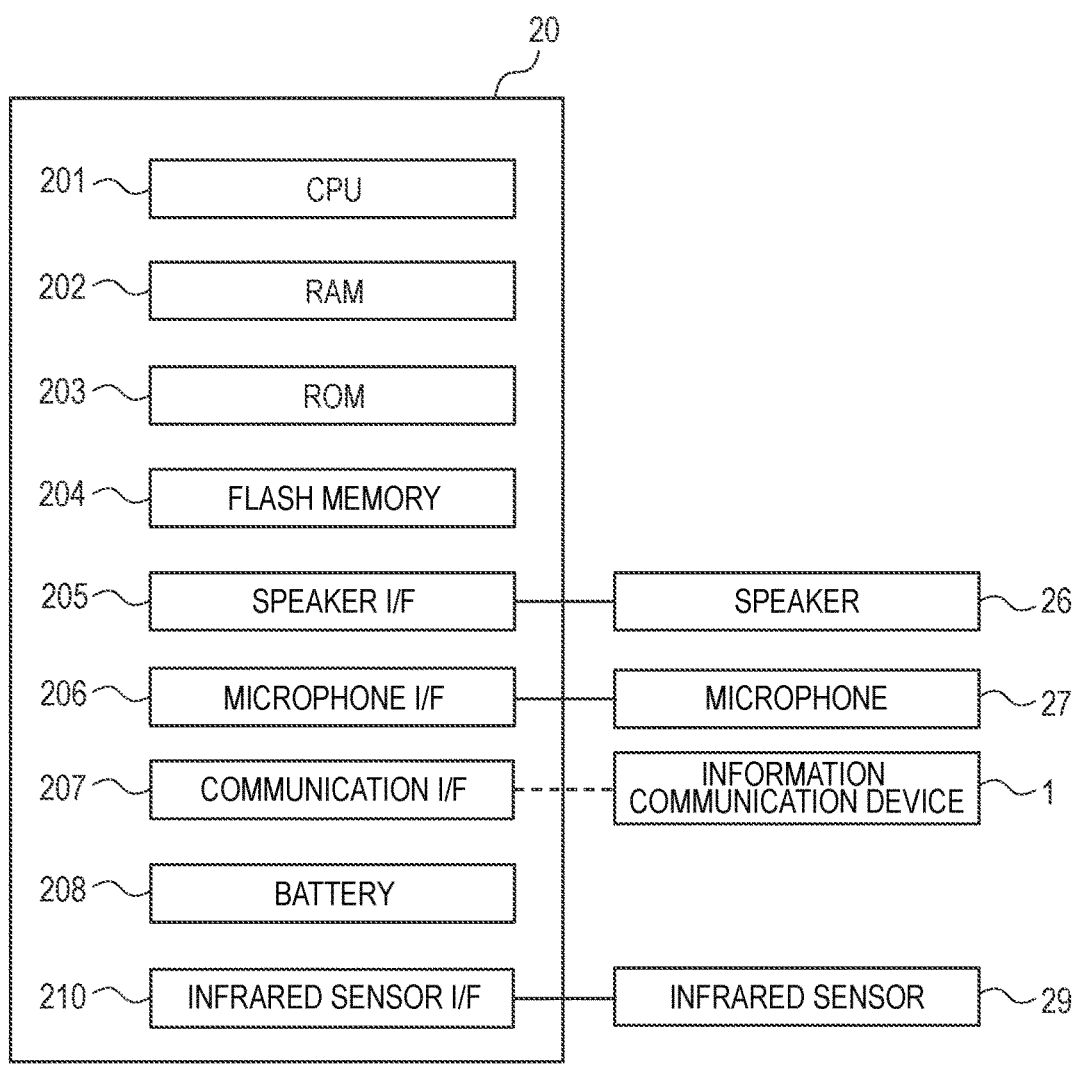
FIG. 2 is a block diagram illustrating a hardware configuration of an earphone according to the first example embodiment.

FIG. 2 is a block diagram illustrating a hardware configuration example of the earphone control device 20. The earphone control device 20 includes a central processing unit (CPU) 201, a random access memory (RAM) 202, a read only memory (ROM) 203, and a flash memory 204. The earphone control device 20 also includes a speaker interface (I/F) 205, a microphone I/F 206, a communication I/F 207, a battery 208, and an infrared sensor I/F 210. Note that, each unit of the earphone control device 20 are connected to each other via a bus, wiring, a driving device, or the like (not shown).

The CPU 201 is a processor that has a function of performing a predetermined calculation according to a program stored in the ROM 203, the flash memory 204, or the like, and also controlling each unit of the earphone control device 20. The RAM 202 is composed of a volatile storage medium and provides a temporary memory area required for the operation of the CPU 201. The ROM 203 is composed of a non-volatile storage medium and stores necessary information such as a program used for the operation of the earphone control device 20. The flash memory 204 is a storage device configured from a non-volatile storage medium and temporarily storing data, storing an operation program of the earphone control device 20, or the like.

The communication I/F 207 is a communication interface based on standards such as Bluetooth (registered trademark) and Wi-Fi (registered trademark), and is a module for performing communication with the information communication device 1.

The speaker I/F 205 is an interface for driving the speaker 26. The speaker I/F 205 includes a digital-to-analog conversion circuit, an amplifier, or the like. The speaker I/F 205 converts the audio data into an analog signal and supplies the analog signal to the speaker 26. Thus, the speaker 26 emits sound waves based on the audio data.

The microphone I/F 206 is an interface for acquiring a signal from the microphone 27. The microphone I/F 206 includes an analog-to-digital conversion circuit, an amplifier, or the like. The microphone I/F 206 converts an analog signal generated by a sound wave received by the microphone 27 into a digital signal. Thus, the earphone control device 20 acquires audio data based on the received sound waves.

The battery 208 is, for example, a secondary battery, and supplies power necessary for the operation of the earphone 2. Since the battery 208 is built in the earphone 2, the earphone 2 can operate wirelessly without wired connection to an external power source.

The infrared sensor I/F 210 is an interface for acquiring a signal from the infrared sensor 29. The infrared sensor I/F 210 includes an analog-to-digital conversion circuit, an amplifier, or the like. The infrared sensor I/F 210 converts an analog signal generated by infrared rays received by the infrared sensor 29 into a digital signal. Thus, the earphone control device 20 acquires detection data of the user 3 based on the received infrared ray.

Note that the hardware configuration illustrated in FIG. 2 is an example, and devices other than these may be added or some devices may not be provided. Further, some devices may be replaced with another device having similar functions. For example, the earphone 2 may further be provided with an input device such as a button so as to be able to receive an operation by the user 3, and further provided with a display device such as a display or a display lamp for providing information to the user 3. Thus, the hardware configuration illustrated in FIG. 2 can be appropriately changed.

Figure 3:
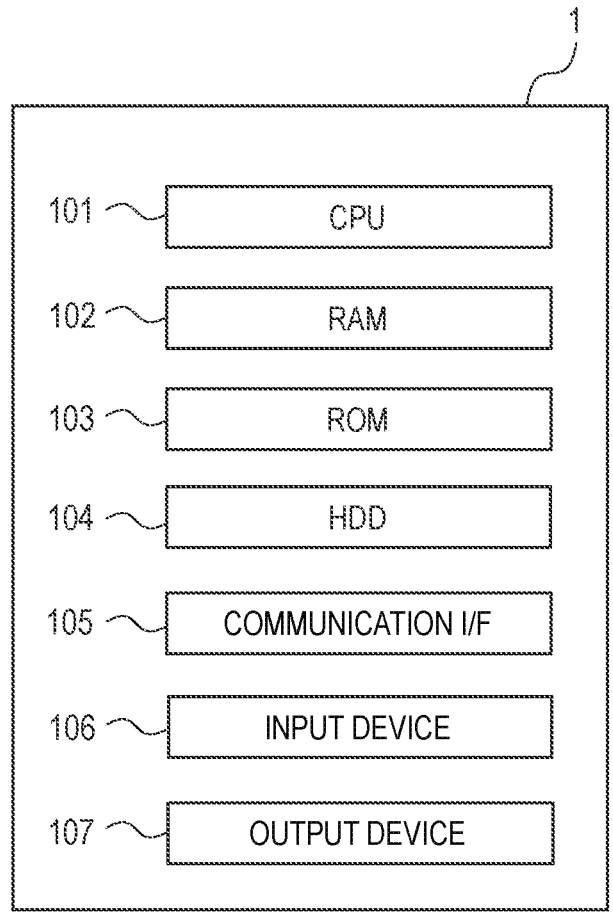
FIG. 3 is a block diagram illustrating a hardware configuration of an information communication device according to the first example embodiment.

FIG. 3 is a block diagram illustrating a hardware configuration example of the information communication device 1. The information communication device 1 includes a CPU 101, a RAM 102, a ROM 103, and a hard disk drive (HDD) 104. The information communication device 1 also includes a communication I/F 105, an input device 106, and an output device 107. Note that, each unit of the information communication device 1 is connected to each other via a bus, wiring, a driving device, or the like (not shown).

In FIG. 3, each unit constituting the information communication device 1 is illustrated as an integrated device, but some of these functions may be provided by an external device. For example, the input device 106 and the output device 107 may be external devices other than the unit constituting functions of a computer including the CPU 101 or the like.

The CPU 101 is a processor that has a function of performing a predetermined calculation according to a program stored in the ROM 103, the HDD 104, or the like, and also controlling each unit of the information communication device 1. The RAM 102 is composed of a volatile storage medium and provides a temporary memory area required for the operation of the CPU 101. The ROM 103 is composed of a non-volatile storage medium and stores necessary information such as a program used for the operation of the information communication device 1. The HDD 104 is a storage device configured from a non-volatile storage medium and temporarily storing data sent to and received from the earphone 2, storing an operation program of the information communication device 1, or the like.

The communication I/F 105 is a communication interface based on standards such as Bluetooth (registered trademark) and Wi-Fi (registered trademark), and is a module for performing communication with the other devices such as the earphone 2.

The input device 106 is a keyboard, a pointing device, or the like, and is used by the user 3 to operate the information communication device 1. Examples of the pointing device include a mouse, a trackball, a touch panel, and a pen tablet.

The output device 107 is, for example, a display device. The display device is a liquid crystal display, an organic light emitting diode (OLED) display, or the like, and is used for displaying information, graphical user interface (GUI) for operation input, or the like. The input device 106 and the output device 107 may be integrally formed as a touch panel.

Note that, the hardware configuration illustrated in FIG. 3 is an example, and devices other than these may be added or some devices may not be provided. Further, some devices may be replaced with other devices having similar functions. Further, some of the functions of the example embodiment may be provided by another device via a network, or the functions of the example embodiment may be realized by being distributed to a plurality of devices. For example, the HDD 104 may be replaced with a solid state drive (SSD) using a semiconductor memory, or may be replaced with a cloud storage. Thus, the hardware configuration illustrated in FIG. 3 can be appropriately changed.

Figure 4:
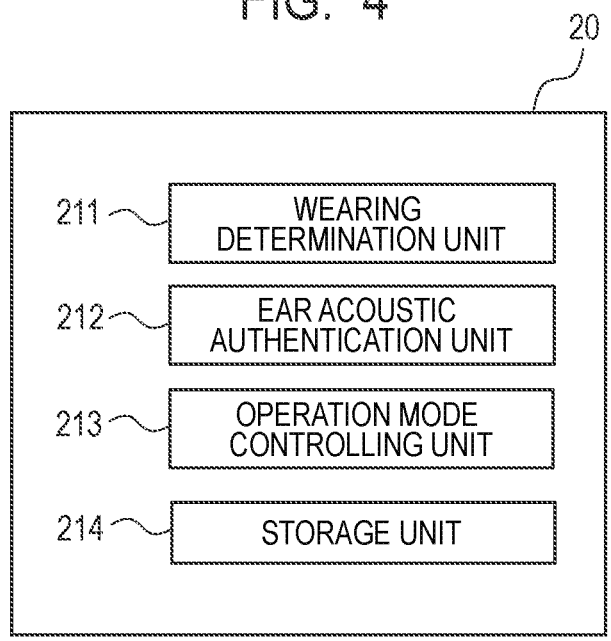
FIG. 4 is a functional block diagram of an earphone control device according to the first example embodiment.

FIG. 4 is a functional block diagram of the earphone control device 20 according to the example embodiment. The earphone control device 20 includes a wearing determination unit 211, an ear acoustic authentication unit 212, an operation mode controlling unit 213, and a storage unit 214.

The CPU 201 loads programs stored in the ROM 203, the flash memory 204, or the like into the RAM 202 and executes them. Thus, the CPU 201 realizes the functions of the wearing determination unit 211, the ear acoustic authentication unit 212, and operation mode controlling unit 213. Further, the CPU 201 controls the flash memory 204 based on the program to realize the function of the storage unit 214. The specific process performed in each of these units will be described later.

In the example embodiment, each function of the function blocks shown in FIG. 4 is provided in the earphone control device 20, but a part of the functions of the function blocks shown in FIG. 4 may be provided in the information communication device 1. That is, each function described above may be realized by the earphone control device 20, may be realized by the information communication device 1, or may be realized by cooperation between the information communication device 1 and the earphone control device 20. The information communication device 1 and the earphone control device 20 are sometimes generally referred to as information processing devices.

Figure 5:
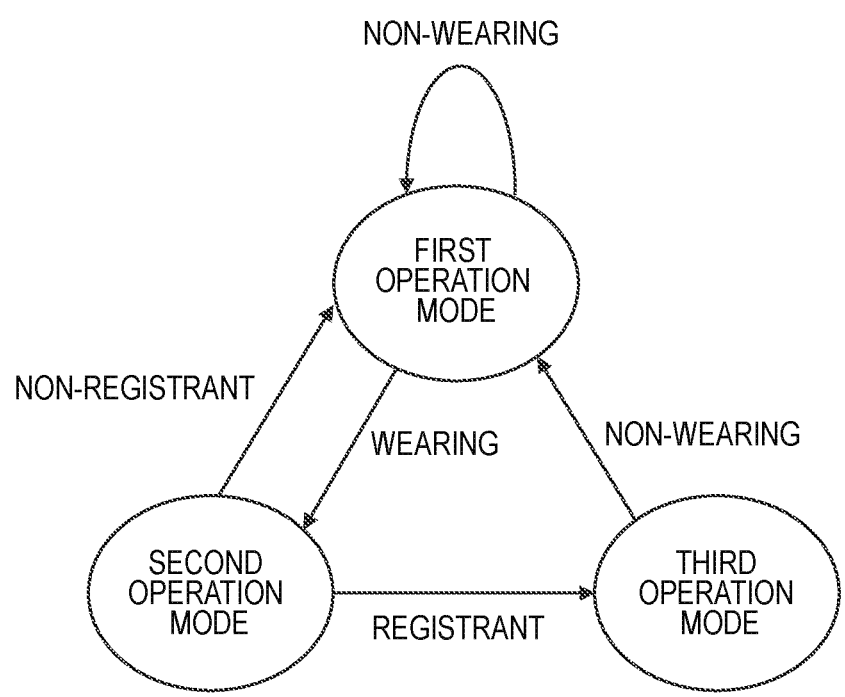
FIG. 5 is a state transition diagram of the earphone according to the first example embodiment.

FIG. 5 is a state transition diagram of the earphone 2 according to the example embodiment. First, with reference to FIG. 5, an outline of the operation of the earphone control device 20 will be described.

The earphone 2 is operable in three modes of a first operation mode, a second operation mode and a third operation mode, and the transition between the modes is controlled by an operation mode controlling unit 213 of an earphone control device 20. The presence or absence of the restrictions of the function which the earphone can execute is different between the respective operation modes. The first operation mode and the second operation mode are operation modes for wearing determination of the earphone 2 and for biometric authentication, respectively. In these modes, the original function of the earphone 2 (hearing of voice or the like) is restricted.

In the first operation mode, the wearing determination unit 211 can determine whether or not the user 3 wears the earphone 2. When the user 3 wears the earphone 2, the infrared ray emitted from the user 3 is made incident on the infrared sensor 29, so that the intensity of the infrared ray received by the infrared sensor 29 is increased. Therefore, the wearing determination unit 211 can determine wearing or non-wearing based on the digital signal indicating the intensity of the infrared ray received by the infrared sensor 29. The determination criteria by the wearing determination unit 211 may be, for example, a determination that the user 3 wears the earphone 2 when the intensity of infrared rays is equal to or greater than a threshold. Alternatively, the determination criteria may be a determination that the user wears the earphone 2 when a wearing score based on the intensity of the infrared ray or a change thereof is calculated and the wearing score is equal to or greater than a threshold.

In a first operation mode, when the wearing determination unit 211 determines that the user 3 wears the earphone 2, the operation mode controlling unit 213 causes the operation mode of the earphone 2 to transit to a second operation mode. In the first operation mode, when the wearing determination unit 211 determines that the user 3 does not wear the earphone 2, the operation mode controlling unit 213 maintains the operation mode of the earphone 2 in the first operation mode.

However, in the first operation mode, the function of the ear acoustic authentication by the ear acoustic authentication unit 212 is restricted, and the ear acoustic authentication is not executable. The second operation mode is an operation mode in which ear acoustic authentication is executable. In other words, the operation mode controlling unit 213 causes the operation mode of the earphone 2 to transit from the first operation mode to the second operation mode to cancel the functional restrictions of the ear acoustic authentication.

In the second operation mode, the ear acoustic authentication unit 212 can determine whether or not the user 3 is a registrant by ear acoustic authentication. The ear acoustic authentication is a biometric authentication for matching the acoustic characteristics of the ear canal of the user 3. By emitting an inspection sound wave toward the ear canal of the user by the speaker 26 and acquiring the sound wave reflected in the ear canal of the user 3 or the like by the microphone 27, the earphone 2 can acquire acoustic characteristics of the ear canal of the user 3. The ear acoustic authentication unit 212 can determine whether or not the user 3 is a registrant by matching the feature amount extracted from the acquired acoustic characteristics of the ear canal against the feature amount extracted from the acoustic characteristics of the ear canal of the registrant. The registrant is a person who is registered as a regular user of the earphone 2 with acoustic characteristics or feature amount of the ear canal. By performing the authentication, the function of the earphone 2 can be restricted to a person without authority, and the use of the earphone 2 by the person without authority can be prevented.

In the example embodiment, the acoustic characteristics of the ear canal of the registrant are previously stored in the storage unit 214, but the acoustic characteristics of the ear canal of the registrant may be acquired from another device such as the information communication device 1 at the time of authentication.

The acoustic characteristics acquired in the ear acoustic authentication are typically acoustic characteristics resulting from resonance in the ear canal, but may also include acoustic characteristics resulting from echo in tissues surrounding the ear canal, such as the skull. The inspection sound wave may not be directly emitted toward the ear canal, but may be emitted to a part of the head of the user 3 by a bone conduction speaker, for example.

In the second operation mode, when the ear acoustic authentication unit 212 determines that the user 3 is a registrant, the operation mode controlling unit 213 causes the operation mode of the earphone 2 to transit to a third operation mode. In the second operation mode, when the ear acoustic authentication unit 212 determines that the user 3 is not a registrant, the operation mode controlling unit 213 causes the operation mode of the earphone 2 to transit to the first operation mode.

The third operation mode is an operation mode in which the user 3 can use the earphone 2. When the function restrictions of the earphone 2 are canceled in the third operation mode, the user 3 can enjoy the original function of the earphone 2. For example, when the earphone 2 is a telephone device for business command, the earphone 2 can receive the audio data of the business command and emit the voice from the speaker 26 in the third operation mode. The third operation mode may be a mode in which all the functional restrictions of the earphone 2 are canceled. In addition, when the available functions are different for each user, the third operation mode may be a mode in which a part of the function restrictions of the earphone 2 permitted to the authenticated user is canceled.

In the third operation mode, the wearing determination unit 211 may perform wearing detection. In the third operation mode, when the wearing determination unit 211 determines that the user 3 does not wear the earphone 2, the operation mode controlling unit 213 causes the operation mode of the earphone 2 to transit to the first operation mode.

Figure 6:
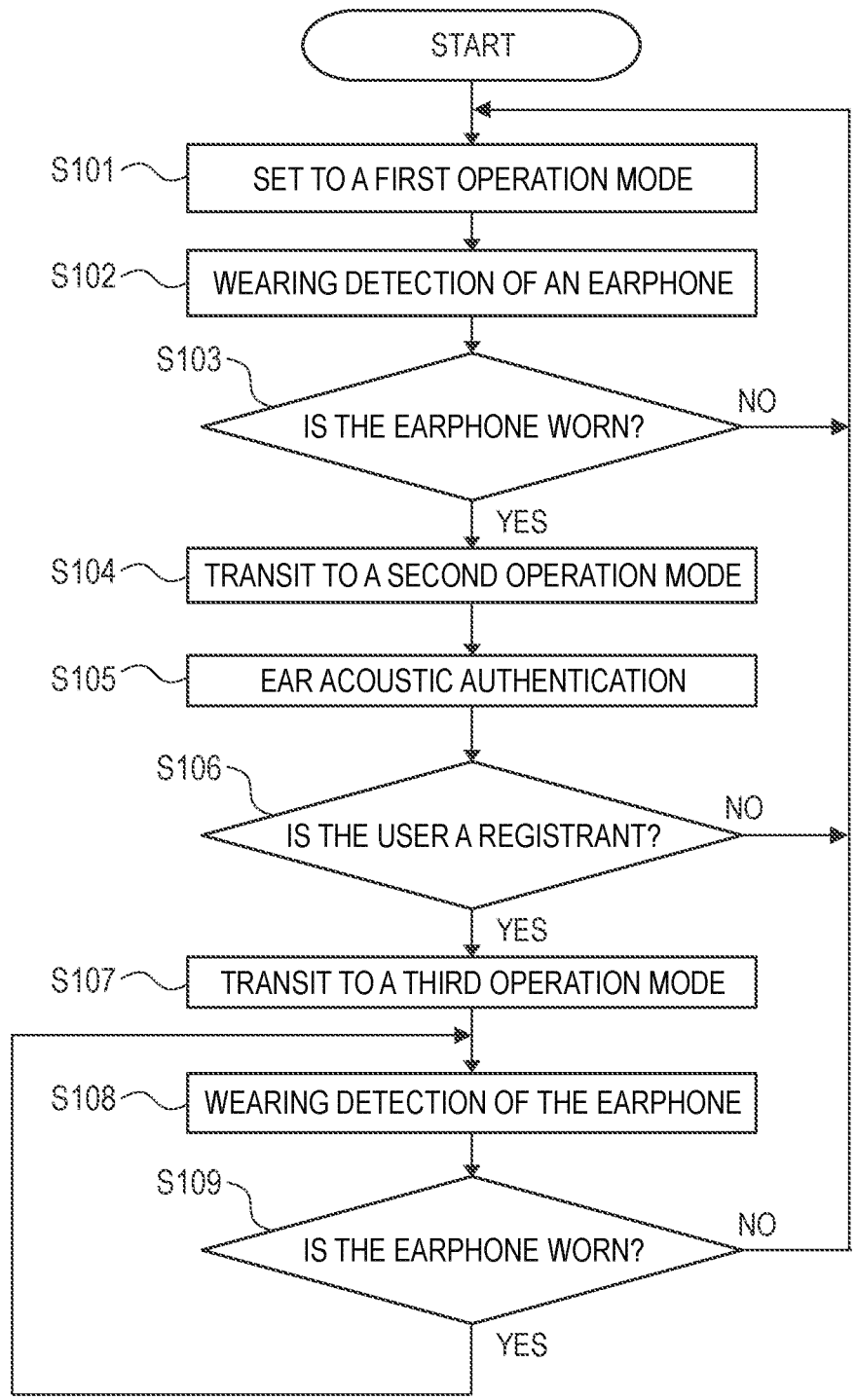
FIG. 6 is a flowchart showing an example of a transition of an operation mode performed by the earphone control device according to the first example embodiment.
Figure 7:
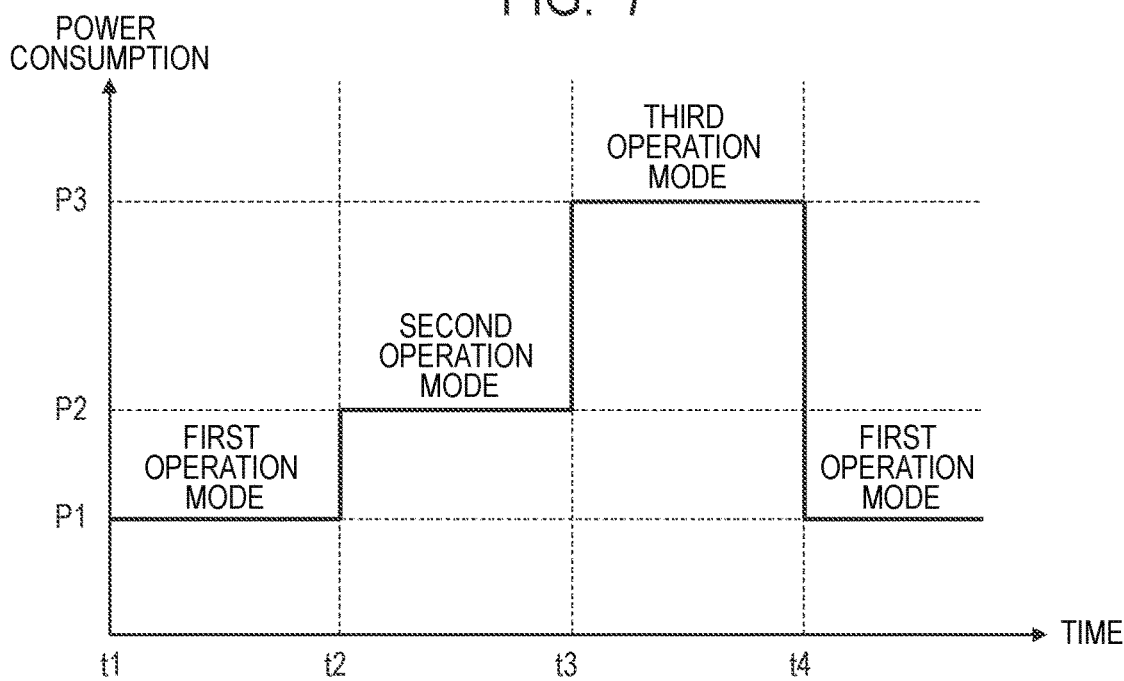
FIG. 7 is a graph showing an example of a change in power consumption of the earphone according to the first example embodiment.

Next, with reference to FIGS. 6 and 7, the transition of the operation mode of the earphone 2 and the change in power consumption accompanying the transition will be described. FIG. 6 is a flowchart showing an example of the transition of the operation mode performed by the earphone control device 20 according to the example embodiment. FIG. 7 is a graph showing an example of a change in power consumption of the earphone 2 according to the example embodiment. FIGS. 6 and 7 show typical processes when the user 3 wears and uses the earphone 2, but the flow may be different from that shown in the figure depending on the state of transition of the operation mode. Note that the scale of this graph is not necessarily accurate, and this graph only schematically shows the change in power consumption accompanying the processes.

The process shown in FIG. 6 is executed, for example, every time a predetermined time elapses when the power of the earphone 2 is on. Alternatively, the process of FIG. 6 may be executed when the user 3 starts using the earphone 2 by operating the earphone 2.

In step S101, the operation mode controlling unit 213 sets the operation mode of the earphone 2 to the first operation mode. The process time in step S101 corresponds to time t1 in FIG. 7. As shown in FIG. 7, at time t1, the power consumption of the earphone 2 is P1.

In step S102, the wearing determination unit 211 performs a process for wearing determination. The process for wearing determination may include acquiring data indicating the intensity of the infrared rays described above.

In step S103, the wearing determination unit 211 determines whether or not the user 3 wears the earphone 2. If it is determined that the user 3 wears the earphone 2 (YES in step S103), the process proceeds to step S104. If it is determined that the user 3 does not wear the earphone 2 (NO in step S103), the process returns to step S101 and the operation mode is maintained in the first operation mode.

In step S104, the operation mode controlling unit 213 causes the operation mode of the earphone 2 to transit to the second operation mode. The process time in step S104 corresponds to time t2 in FIG. 7. As shown in FIG. 7, at time t2, the power consumption of the earphone 2 changes from P1 to P2, of which the power consumption is greater than that of P1.

The difference in power consumption between the first operation mode and the second operation mode will be described. As described above, the second operation mode is different from the first operation mode in that ear acoustic authentication is executable. The ear acoustic authentication includes, for example, an arithmetic processing for extracting a feature amount from the data of the acoustic characteristics, and a processing for matching the feature amount. In this case, the power consumption required for the ear acoustic authentication is {(calculation amount of the feature extraction+calculation amount of the matching)×power consumption per calculation amount unit}. Since the earphone 2 is a wireless device, the power is supplied from the built-in battery 208, and since the earphone 2 is a small device worn on the ear, considering that the power capacity of the battery 208 is not so large, this power consumption is too large to be ignored. Therefore, in the second operation mode, the power consumption of the earphone 2 is increased more than in the first operation mode.

In step S105, the ear acoustic authentication unit 212 performs a process for ear acoustic authentication. The processing for ear acoustic authentication may include acquisition of acoustic characteristics of the ear canal, extraction of feature amount, matching of feature amount, or the like.

In step S106, the ear acoustic authentication unit 212 determines whether or not the user 3 is a registrant. If it is determined that the user 3 is the registrant (YES in step S106), the process proceeds to step S107. If it is determined that the user 3 is not the registrant (NO in step S106), the process returns to step S101, and the operation mode transits to the first operation mode.

In step S107, the operation mode controlling unit 213 causes the operation mode of the earphone 2 to transit to the third operation mode. The process time in step S107 corresponds to time t3 in FIG. 7. As shown in FIG. 7, at time t3, the power consumption of the earphone 2 changes from P2 to P3, of which power consumption is greater than that of P2. In the third operation mode, since processing such as communication of audio data between the information communication device 1 and the earphone 2 and transmission of sound waves by the speaker 26 are performed, power consumption is further increased than in the second operation mode.

In steps S108 and S109, the wearing detection of the earphone 2 is performed in the same manner as in steps S102 and S103. When it is determined that the user 3 wears the earphone 2 (YES in step S109), the operation mode is maintained in the third operation mode, and thereafter, wearing detection processing is performed at predetermined intervals. If it is determined that the user 3 does not wear the earphone 2 (NO in step S109), the process returns to step S101, and the operation mode transits to the first operation mode. As a possibility of determining that the earphone 2 is not worn after the completion of the authentication, for example, a case in which the user 3 stops or ends the use of the earphone 2 and removes the earphone 2 is assumed. In this case, by the operation mode transiting to the first operation mode, the function of the earphone 2 is restricted so that the earphone 2 is not used by others.

The time at which it is determined in step S109 that the user 3 does not wear the earphone 2 corresponds to time t4 in FIG. 7. As shown in FIG. 7, at time t4, the power consumption of the earphone 2 changes from P3 to P1, of which power consumption is less than that of P3.

An earphone control device 20 of the example embodiment can switch an operation mode of the earphone 2 between a first operation mode in which processing for ear acoustic authentication is not executable and a second operation mode in which processing for ear acoustic authentication is executable. In the example embodiment, since the switching of the operation mode is performed based on the result of the wearing determination, the control of not performing the ear acoustic authentication when the person does not wear the earphone 2 is realized. Thus, power consumption caused by the ear acoustic authentication of the earphone is reduced. Therefore, according to example embodiment, an information processing device capable of reducing power consumption in a wearable device for performing biometric authentication based on acoustic characteristics is provided.

Since the earphone 2 is typically a wireless wearable device worn on the ear, the power capacity of the battery 208 for driving the earphone 2 is small. Therefore, it is effective to reduce power consumption by the above control, and the time capable of using the earphone 2 can be prolonged.

Second Example Embodiment

The information processing system of the example embodiment is different from that of the first example embodiment in that a part of the processing of the ear acoustic authentication is performed outside the earphone 2. Hereinafter, the difference from first example embodiment is mainly described, and the description of the common parts is omitted or simplified.

Figure 8:
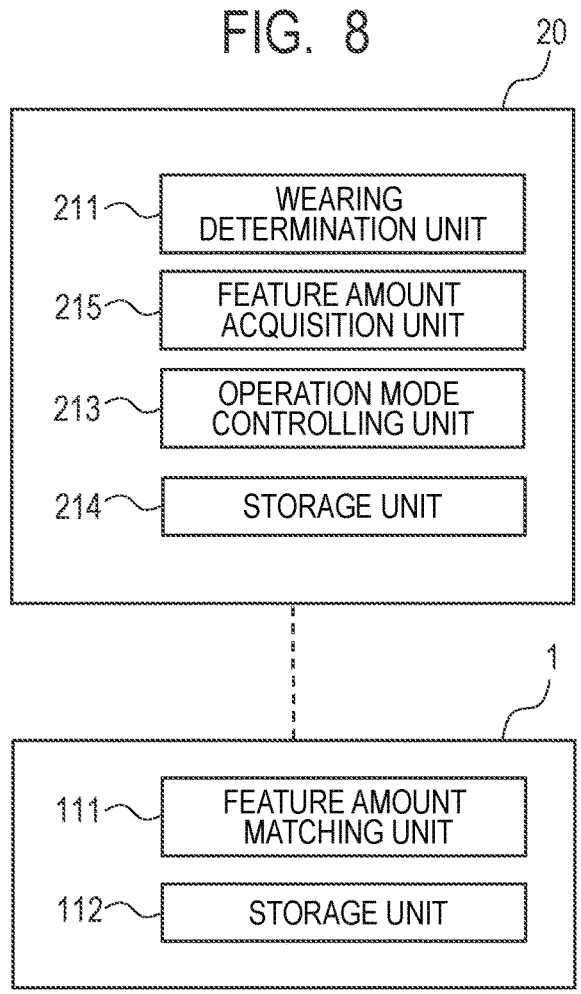
FIG. 8 is a functional block diagram of an earphone control device and an information communication device according to a second example embodiment.

FIG. 8 is a functional block diagram of the earphone control device 20 and the information communication device 1 according to the example embodiment. The earphone control device 20 includes a feature amount acquisition unit 215 instead of an ear acoustic authentication unit 212 of the first example embodiment. The information communication device 1 includes a feature amount matching unit 111 and a storage unit 112.

A CPU 201 of an earphone control device 20 realizes the function of a feature amount acquisition unit 215 by executing programs stored in a ROM 203, a flash memory 204, or the like. The CPU 101 of the information communication device 1 executes a program stored in the ROM 103, the HDD 104, or the like to realize the function of the feature amount matching unit 111. The CPU 101 controls the HDD 104 based on the program to realize the function of the storage unit 112. The specific processing performed by each of these units will be described later.

Figure 9:
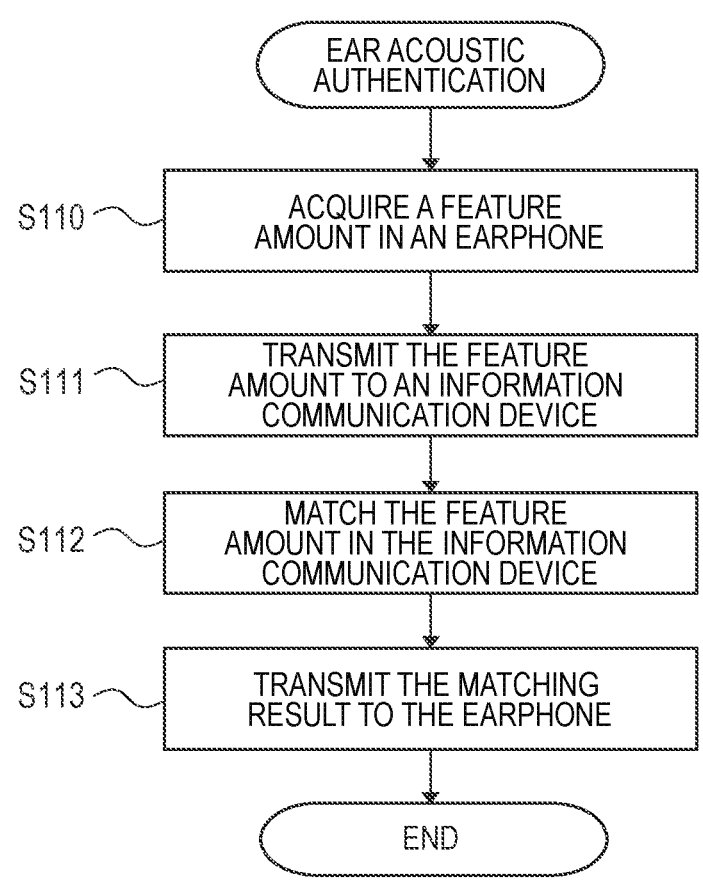
FIG. 9 is a flowchart showing a process of an ear acoustic authentication according to the second example embodiment.

FIG. 9 is a flowchart showing the processing of the ear acoustic authentication according to the example embodiment. The processing of FIG. 9 shows the processing of step S105 in FIG. 6 according to first example embodiment in more detail. The other processes are the same as those in FIG. 6, and therefore description thereof will be omitted.

In step S110, the feature amount acquisition unit 215 of the earphone control device 20 acquires the acoustic characteristics of the ear canal of the user 3 and extracts the feature amount from the acoustic characteristics. Thus, the feature amount acquisition unit 215 acquires a feature amount based on the acoustic characteristics of the ear canal of the user 3.

In step S111, the earphone 2 transmits the feature amount to the information communication device 1. The information communication device 1 stores the acquired feature amount in the storage unit 112.

In step S112, the feature amount matching unit 111 of the information communication device 1 matches the feature amount of the user 3 against the feature amount of the registrant stored in the storage unit 112 in advance.

In step S113, the information communication device 1 transmits the matching result to the earphone 2. The CPU 201 of the earphone 2 performs the branch processing of step S106 in FIG. 6 using the matching result.

In the example embodiment, the matching processing among the processing of the ear acoustic authentication is performed by an information communication device 1 outside the earphone 2. Even in the configuration, ear acoustic authentication can be performed in the same manner as in the first example embodiment. Accordingly, an information processing device capable of reducing power consumption in a wearable device for performing biometric authentication based on acoustic characteristics as in the case of the first example embodiment is provided.

There are advantages and disadvantages in a configuration in which the ear acoustic authentication is performed by the earphone 2 as in the case of the first example embodiment and a configuration in which the matching processing among the ear acoustic authentication processing is performed by a device outside the earphone 2 as in the case of the second example embodiment. Therefore, it is desirable to appropriately select the two configurations according to the required specifications. Advantages and disadvantages of both are described below.

In the configuration of the first example embodiment, since the processing of the ear acoustic authentication is completed within the earphone 2, there is no need to communicate with other devices at the time of ear acoustic authentication, and it may be advantageous in that power consumption caused by the communication may be reduced. On the other hand, in the configuration of the first example embodiment, it is necessary to store the feature amount of the registrant in advance in the earphone 2, and when a matching algorithm with a large calculation amount is used, it may be disadvantageous in that the power consumption may be increased.

In the configuration of the second example embodiment, the power consumption required for the ear acoustic authentication is (calculation amount for feature amount extraction×power consumption per calculation amount unit+communication amount for feature amount transmission×power consumption per communication amount unit). Therefore, in a case where the power consumption amount required for communication is less than the power consumption amount required for matching, the second example embodiment configuration may reduce the power consumption amount. Further, in the configuration of the second example embodiment, it is not necessary to store the feature amount of the registrant in the earphone 2 in advance, and since the registrant is managed by the host device, it may be advantageous in that it is easy to deal with the case in which the user is unspecified or the user is updated. On the other hand, when the communication amount is large, the power consumption is larger than the configuration of the first example embodiment, and since communication is essential, it may be disadvantageous in that the earphone 2 cannot be used at the time of communication failure.

Third Example Embodiment

The information processing system of the example embodiment differs from the first example embodiment or the second example embodiment in that the processing of the ear acoustic authentication can be performed both inside and outside the earphone 2. The differences between the first example embodiment or the second example embodiment are mainly described below, and the description of the common parts is omitted or simplified.

Figure 10:
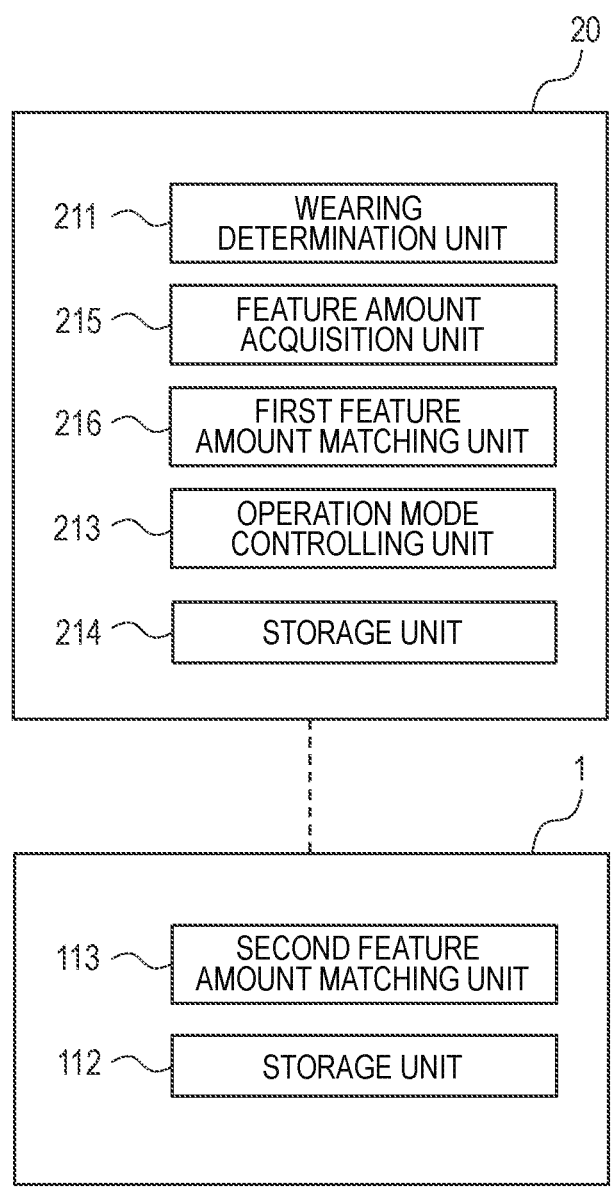
FIG. 10 is a functional block diagram of an earphone control device and an information communication device according to a third example embodiment.

FIG. 10 is a functional block diagram of the earphone control device 20 and the information communication device 1 according to the example embodiment. In addition to the configuration shown in FIG. 8, the earphone control device 20 includes a first feature amount matching unit 216. The information communication device 1 includes a second feature amount matching unit 113 instead of the feature amount matching unit 111 shown in FIG. 8.

A CPU 201 of an earphone control device 20 realizes the function of a first feature amount matching unit 216 by executing programs stored in a ROM 203, a flash memory 204, or the like. The CPU 101 of the information communication device 1 executes a program stored in the ROM 103, the HDD 104, or the like to realize the function of the second feature amount matching unit 113. The specific processing performed by each of these units will be described later.

Figure 11:
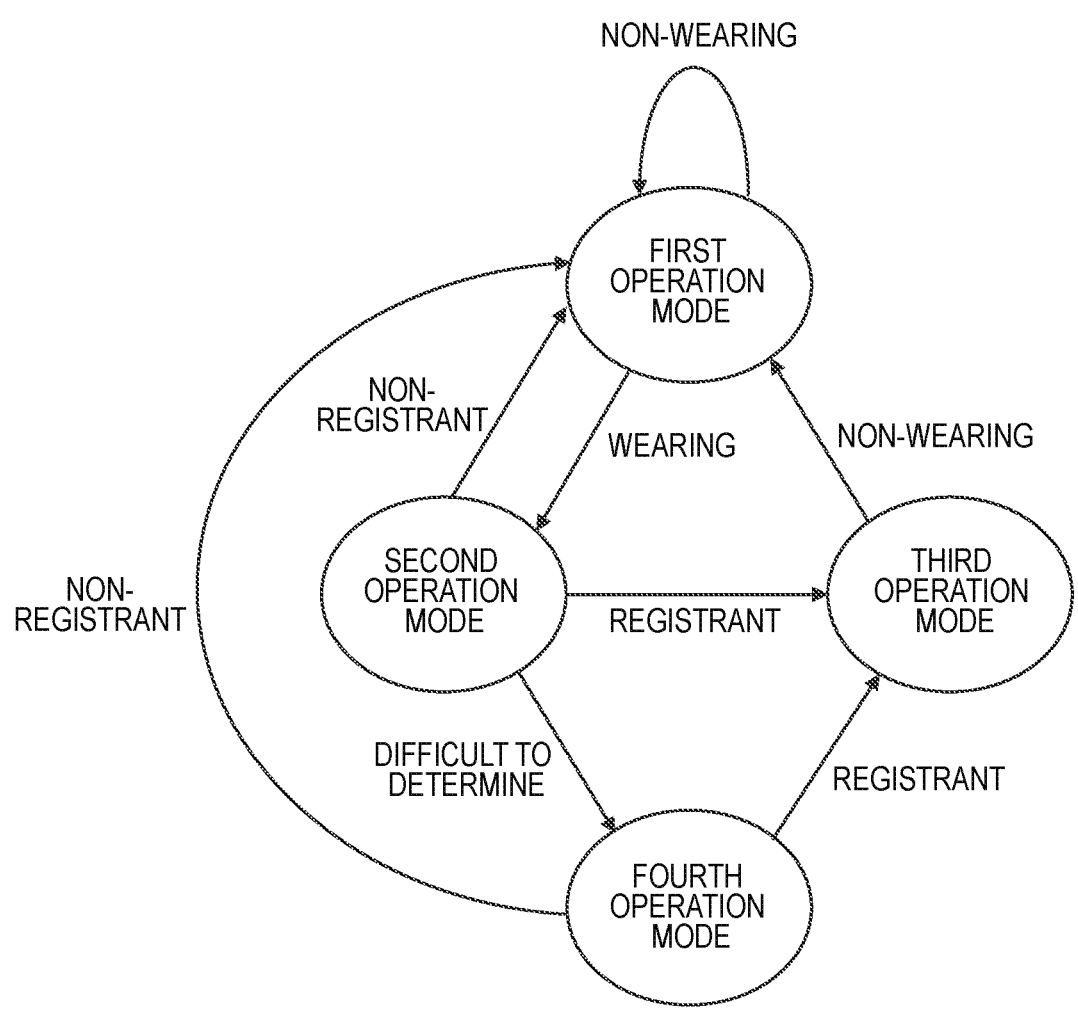
FIG. 11 is a state transition diagram of an earphone according to the third example embodiment.

FIG. 11 is a state transition diagram of the earphone 2 according to the example embodiment. First, with reference to FIG. 11, an outline of the operation of the earphone control device 20 will be described. The difference from the state transition diagram shown in FIG. 5 is that a fourth operation mode is further added.

In the example embodiment, a second operation mode is an operation mode in which a matching processing for ear acoustic authentication (first biometric authentication) can be performed in the earphone 2, and a fourth operation mode is an operation mode in which a matching processing for ear acoustic authentication (second biometric authentication) can be performed in the information communication device 1. The algorithm of the second biometric authentication in the information communication device 1 is more accurate than the algorithm of the first biometric authentication in the earphone 2, but the power consumption is greater.

In the second operation mode, the feature amount acquisition unit 215 acquires the feature amount by extracting the feature amount from the acoustic characteristics of the ear canal of the user 3. A first feature amount matching unit 216 matches the feature amount of the user 3 acquired by the feature amount acquisition unit 215 against the feature amount of the registrant to determine whether the user 3 is a registrant or not.

In a second operation mode, when a first feature amount matching unit 216 determines that the user 3 is a registrant, an operation mode controlling unit 213 causes an operation mode of the earphone 2 to transit to a third operation mode. In the second operation mode, when the first feature amount matching unit 216 determines that the user 3 is not a registrant, an operation mode controlling unit 213 causes the operation mode of the earphone 2 to transit to the first operation mode. On the other hand, when it is difficult to determine whether or not the user 3 is a registrant in the second operation mode, the operation mode controlling unit 213 cause the operation mode of the earphone 2 to transit to the fourth operation mode. The case in which the determination is difficult is, for example, the case in which the score indicating the similarity between the two feature amounts is near a threshold for determining whether or not the user is a registrant. In such a case, since it is desirable to perform the matching with higher accuracy, the operation mode of the earphone 2 transits to a fourth operation mode in which the matching with higher accuracy is executable.

In the fourth operation mode, the second feature amount matching unit 113 acquires the feature amount of the user 3 from the earphone 2 and matches the feature amount of the user 3 against the feature amount of a registrant to determine whether the user 3 is a registrant or not.

In the fourth operation mode, when the second feature amount matching unit 113 determines that the user 3 is a registrant, the operation mode controlling unit 213 causes an operation mode of the earphone 2 to transit to a third operation mode. In a fourth operation mode, when a second feature amount matching unit 113 determines that the user 3 is not a registrant, an operation mode controlling unit 213 causes the operation mode of the earphone 2 to transit to a first operation mode.

Figure 12:
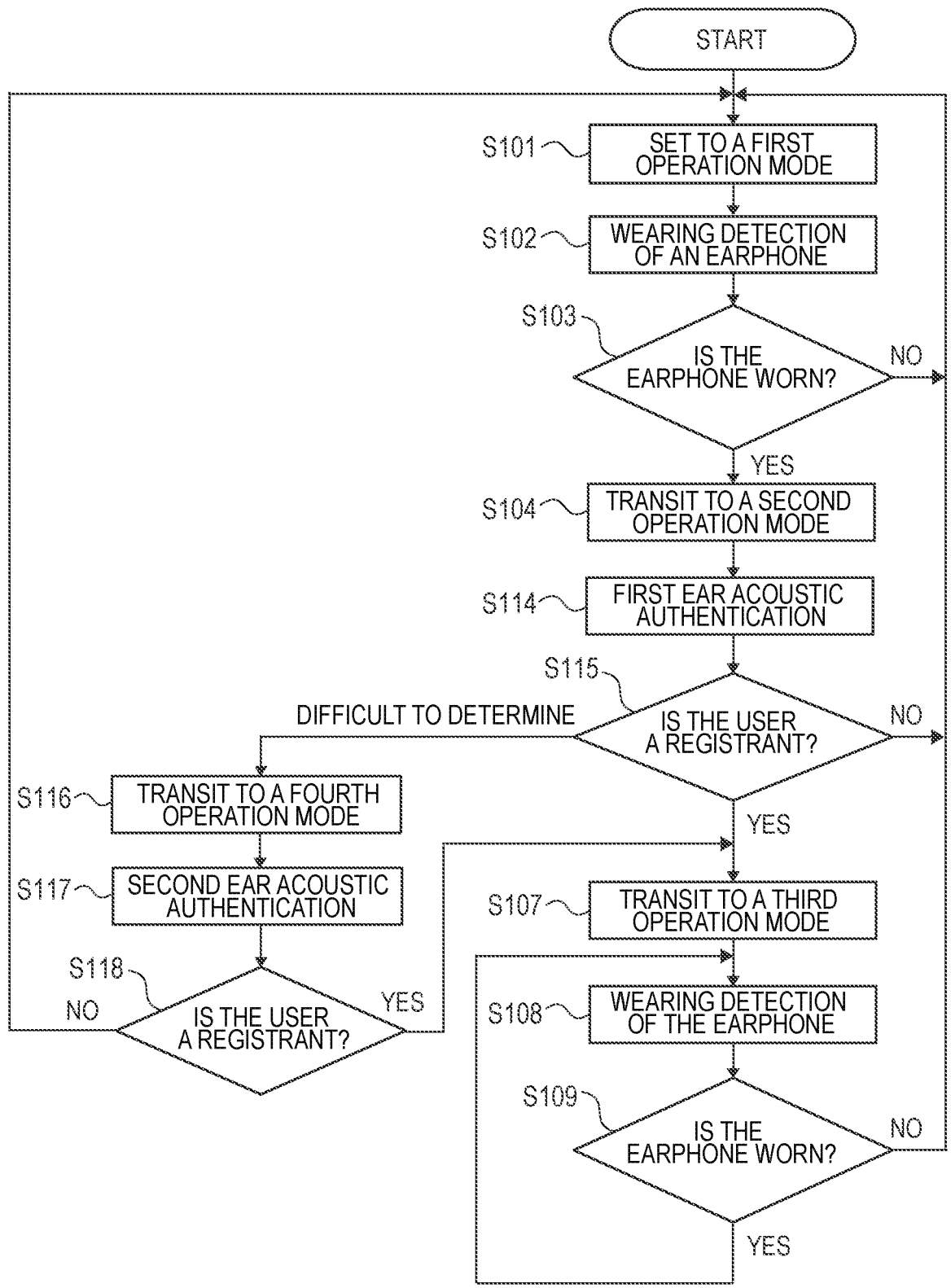
FIG. 12 is a flowchart showing an example of a transition of an operation mode performed by the earphone control device according to the third example embodiment.
Figure 13:
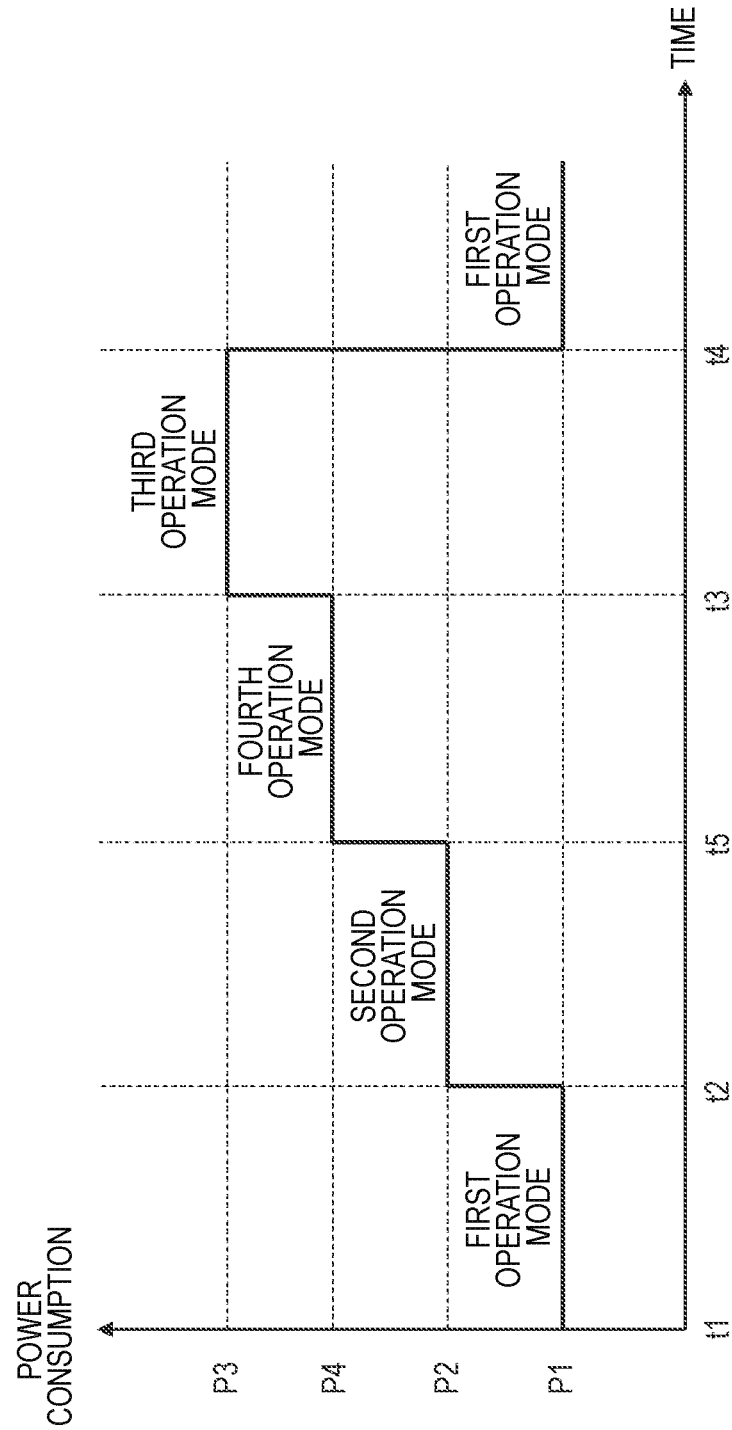
FIG. 13 is a graph showing an example of a change in power consumption of the earphone according to the third example embodiment.

Next, with reference to FIGS. 12 and 13, the transition of the operation mode of the earphone 2 and the change in power consumption accompanying the transition will be described. FIG. 12 is a flowchart showing an example of the transition of the operation mode performed by the earphone control device 20 according to the example embodiment. FIG. 13 is a graph showing an example of a change in power consumption of the earphone 2 according to the example embodiment. FIGS. 12 and 13 show typical processing when the user 3 wears and uses the earphone 2, but the flow may be different from that shown in the figure depending on the state of transition of the operation mode.

In step S114, the feature amount acquisition unit 215 of the earphone control device 20 acquires the acoustic characteristics of the ear canal of the user 3 and extracts the feature amount from the acoustic characteristics. Thus, the feature amount acquisition unit 215 acquires a feature amount based on the acoustic characteristics of the ear canal of the user 3. Thereafter, the first feature amount matching unit 216 matches the feature amount of the user 3 against the feature amount of the registrant stored in the storage unit 214 in advance.

In step S115, the first feature amount matching unit 216 determines whether or not the user 3 is a registrant. If it is determined that the user 3 is the registrant (YES in step S115), the process proceeds to step S107. If it is determined that the user 3 is not the registrant (NO in step S115), the process returns to step S101, and the operation mode transits to the first operation mode. If it is difficult to determine whether or not the user 3 is a registrant ("DIFFICULT TO DETERMINE" in step S115), the process proceeds to step S116.

In step S116, the operation mode controlling unit 213 causes the operation mode of the earphone 2 to transit to the fourth operation mode. The process time in step S116 corresponds to time t5 in FIG. 13. As shown in FIG. 13, at time t5, the power consumption of the earphone 2 changes from P2 to P4, of which power consumption is greater than that of P2. The reason for the increase in power consumption is that the second ear acoustic authentication is a process requiring communication and requires more power than the first ear acoustic authentication.

In step S117, the earphone 2 and the information communication device 1 perform second ear acoustic authentication. This processing is similar to the processing of steps S111 to S113 in FIG. 9. That is, in the second ear acoustic authentication, the second feature amount matching unit 113 acquires the feature amount from the earphone 2 and matches the feature amount of the user 3 against the feature amount of the registrant. The matching result is transmitted from the information communication device 1 to the earphone 2. In this way, the information communication device 1 performs the matching processing, which is a difference from the first ear acoustic authentication in the second ear acoustic authentication.

A CPU 201 of the earphone 2 performs branch processing of a step S118 by using the matching result. If it is determined that the user 3 is the registrant (YES in step S118), the process proceeds to step S107. If it is determined that the user 3 is not the registrant (NO in step S118), the process returns to step S101, and the operation mode transits to the first operation mode.

In the example embodiment, the matching processing of the first ear acoustic authentication is performed in the earphone 2, and the matching processing of the second ear acoustic authentication is performed in the information communication device 1. Even in the configuration, ear acoustic authentication can be performed in the same manner as in the first example embodiment. Accordingly, an information processing device capable of reducing power consumption in a wearable device for performing biometric authentication based on acoustic characteristics as in the case of the first example embodiment is provided. In the example embodiment, the configuration in which the matching is performed in the earphone 2 as in the first example embodiment and the configuration in which the matching is performed in the information communication device 1 as in the second example embodiment are combined. Then, the information communication device 1 performs matching with high accuracy only when it is difficult to determine by low power consumption and simple matching in the earphone 2, so that both reduction in power consumption and securing of authentication accuracy can be achieved.

The system described in the above example embodiment can also be configured as the following fourth example embodiment.

Fourth Example Embodiment

Figure 14:
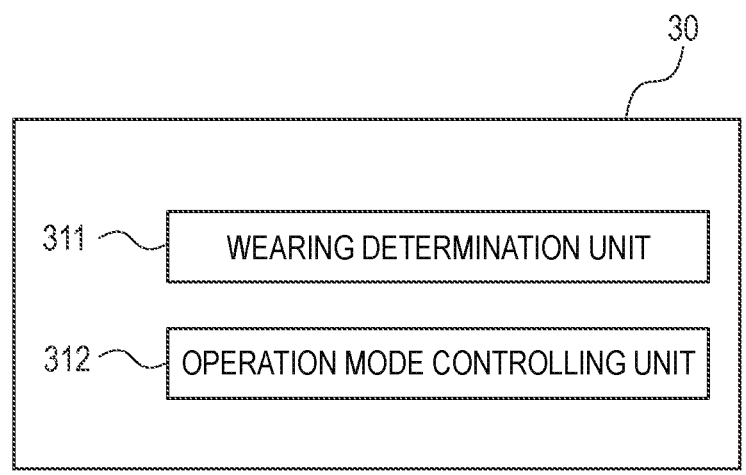
FIG. 14 is a functional block diagram of an information processing device according to a fourth example embodiment.

FIG. 14 is a functional block diagram of the information processing device 30 according to the fourth example embodiment. The information processing device 30 includes a wearing determination unit 311 and an operation mode controlling unit 312. The wearing determination unit 311 determines whether or not a user wears a wearable device that emits a sound wave to perform a biometric authentication based on acoustic characteristics toward a part of a head of the user. The operation mode controlling unit 312 switches, based on a result of a determination by the wearing determination unit 311, an operation mode of the wearable device between a plurality of operation modes including a first operation mode in which a process for the biometric authentication is not executable and a second operation mode in which a process for the biometric authentication is executable.

According to example embodiment, an information processing device 30 capable of reducing power consumption in a wearable device for performing biometric authentication based on acoustic characteristics is provided.

Modified Example Embodiments

The disclosure is not limited to the example embodiments described above, and may be suitably modified within the scope of the disclosure. For example, an example in which a part of the configuration of one embodiment is added to another embodiment or an example in which a part of the configuration of another embodiment is replaced is also an example embodiment.

In the above example embodiment, although the earphone 2 is exemplified as an example of a wearable device, the example embodiment is not limited to a device worn on the ear as long as acoustic information necessary for processing can be acquired. For example, the wearable device may be a bone conduction type acoustic device.

Further, in the example embodiment described above, the infrared sensor 29 is exemplified as the means of wearing determination, but the example embodiment is not limited to this as long as the wearing determination can be made. For example, by emitting sound waves to the ear canal of the user 3 and acquiring acoustic characteristics of the echo sound such as the intensity of the echo sound and the echo time, the wearing determination may be performed based on the acoustic characteristics of the echo sound. In this case, the speaker 26 and the microphone 27 function not only as an ear acoustic authentication but also as a device for wearing determination. Therefore, the device configuration can be simplified.

Further, in the second example embodiment and the third example embodiment, although the feature amount is transmitted from the earphone 2 to the information communication device 1, data of acoustic characteristics of the ear canal may be transmitted. In this case, the information communication device 1 may perform the process of extracting the feature amount. In this example, although the communication amount increases, the calculation amount in the earphone 2 can be reduced.

The scope of each of the example embodiments also includes a processing method that stores, in a storage medium, a program that causes the configuration of each of the example embodiments to operate so as to implement the function of each of the example embodiments described above, reads the program stored in the storage medium as a code, and executes the program in a computer. That is, the scope of each of the example embodiments also includes a computer readable storage medium. Further, each of the example embodiments includes not only the storage medium in which the computer program described above is stored but also the computer program itself. Further, one or two or more components included in the example embodiments described above may be a circuit such as an application specific integrated circuit (ASIC)), a field programmable gate array (FPGA), or the like configured to implement the function of each component.

As the storage medium, for example, a floppy (registered trademark) disk, a hard disk, an optical disk, a magneto-optical disk, a compact disk (CD)-ROM, a magnetic tape, a nonvolatile memory card, or a ROM can be used. Further, the scope of each of the example embodiments includes an example that operates on operating system (OS) to perform a process in cooperation with another software or a function of an add-in board without being limited to an example that performs a process by an individual program stored in the storage medium.

Further, a service implemented by the function of each of the example embodiments described above may be provided to a user in a form of software as a service (SaaS).

It should be noted that the above-described embodiments are merely examples of embodying the example embodiment, and the technical scope of the example embodiment should not be limitedly interpreted by these. That is, the example embodiment can be implemented in various forms without departing from the technical idea or the main features thereof.

The whole or part of the example embodiments disclosed above can be described as, but not limited to, the following supplementary notes.

(Supplementary Note 1)

An information processing device comprising:
  a wearing determination unit configured to determine whether or not a user wears a wearable device that emits a sound wave to perform a biometric authentication based on acoustic characteristics toward a part of a head of the user; and
  an operation mode controlling unit configured to switch, based on a result of a determination by the wearing determination unit, an operation mode of the wearable device between a plurality of operation modes including a first operation mode in which a process for the biometric authentication is not executable and a second operation mode in which a process for the biometric authentication is executable.

(Supplementary Note 2)

The information processing device according to supplementary note 1, wherein a power consumption in the second operation mode is greater than a power consumption in the first operation mode.

(Supplementary Note 3)

The information processing device according to supplementary note 1 or 2, wherein the operation mode controlling unit switches an operation mode of the wearable device from the first operation mode to the second operation mode in a case where it is determined that the user wears the wearable device by the wearing determination unit.

(Supplementary Note 4)

The information processing device according to any one of supplementary notes 1 to 3,
  wherein the plurality of operation modes includes a third operation mode in which the user can use the wearable device, and
  wherein a power consumption in the third operation mode is greater than a power consumption in the second operation mode.

(Supplementary Note 5)

The information processing device according to supplementary note 4, wherein the operation mode controlling unit switches an operation mode of the wearable device from the second operation mode to the third operation mode in a case where the user is recognized to be able to use the wearable device by the biometric authentication.

(Supplementary Note 6)

The information processing device according to any one of supplementary notes 1 to 5, wherein a matching of the acoustic characteristics for the biometric authentication is performed by the wearable device.

(Supplementary Note 7)

The information processing device according to any one of supplementary notes 1 to 5, wherein a matching of the acoustic characteristics for the biometric authentication is performed by a device that is able to communicate with the wearable device.

(Supplementary Note 8)

The information processing device according to any one of supplementary notes 1 to 3,
  wherein the biometric authentication includes a first biometric authentication and a second biometric authentication having higher accuracy than the first biometric authentication,
  wherein the second operation mode is a mode in which a process for the first biometric authentication is executable, and
  wherein the plurality of operation modes further includes a fourth operation mode in which a process for the second biometric authentication is executable.

(Supplementary Note 9)

The information processing device according to supplementary note 8, wherein a power consumption in the fourth operation mode is greater than a power consumption in the second operation mode.

(Supplementary Note 10)

The information processing device according to supplementary note 8 or 9, wherein the operation mode controlling unit switches an operation mode of the wearable device from the second operation mode to the fourth operation mode in a case where it is difficult to determine whether or not the user can use the wearable device by the first biometric authentication.

(Supplementary Note 11)

The information processing device according to any one of supplementary notes 8 to 10,
wherein a matching of the acoustic characteristics for the first biometric authentication is performed by the wearable device, and
wherein a matching of the acoustic characteristics for the second biometric authentication is performed by a device that is able to communicate with the wearable device.

(Supplementary Note 12)

The information processing device according to any one of supplementary notes 8 to 11,
wherein the plurality of operation modes further includes a third operation mode in which the user can use a function of the wearable device, and
wherein a power consumption in the third operation mode is greater than a power consumption in the fourth operation mode.

(Supplementary Note 13)

The information processing device according to supplementary note 12, wherein the operation mode controlling unit switches an operation mode of the wearable device from the second operation mode or the fourth operation mode to the third operation mode in a case where the user is recognized to be able to use the wearable device by the first biometric authentication or the second biometric authentication.

(Supplementary Note 14)

The information processing device according to any one of supplementary notes 1 to 13, wherein the biometric authentication is performed by matching acoustic characteristics of an ear canal.

(Supplementary Note 15)

The information processing device according to any one of supplementary notes 1 to 14, wherein the wearable device is an acoustic device that is worn on an ear of the user.

(Supplementary Note 16)

The information processing device according to any one of supplementary notes 1 to 15, wherein the wearable device is a wireless device that operates by receiving a power supply from a battery built in the wearable device.

(Supplementary Note 17)

A wearable device emitting a sound wave to perform a biometric authentication based on acoustic characteristics toward a part of a head of a user comprising:
a wearing determination unit configured to determine whether or not the user wears the wearable device; and
an operation mode controlling unit configured to switch, based on a result of a determination by the wearing determination unit, an operation mode of the wearable device between a plurality of operation modes including a first operation mode in which a process for the biometric authentication is not executable and a second operation mode in which a process for the biometric authentication is executable.

(Supplementary Note 18)

An information processing method comprising:
determining whether or not a user wears a wearable device that emits a sound wave to perform a biometric authentication based on acoustic characteristics toward a part of a head of the user; and
switching, based on a result of a determination, an operation mode of the wearable device between a plurality of operation modes including a first operation mode in which a process for the biometric authentication is not executable and a second operation mode in which a process for the biometric authentication is executable.

(Supplementary Note 19)

A storage medium storing a program that causes a computer to perform:
determining whether or not a user wears a wearable device that emits a sound wave to perform a biometric authentication based on acoustic characteristics toward a part of a head of the user; and
switching, based on a result of a determination, an operation mode of the wearable device between a plurality of operation modes including a first operation mode in which a process for the biometric authentication is not executable and a second operation mode in which a process for the biometric authentication is executable.

REFERENCE SIGNS LIST 1 information communication device
2 earphone
3 user
20 earphone control device
26 speaker
27 microphone
29 infrared sensor
30 information processing device
101, 201 CPU
102, 202 RAM
103, 203 ROM
104 HDD
105, 207 communication I/F
106 input device
107 output device
111 feature amount matching unit
112, 214 storage unit
113 second feature amount matching unit
204 flash memory
205 speaker I/F
206 microphone I/F
208 battery
210 infrared sensor I/F
211, 311 wearing determination unit
212 ear acoustic authentication unit
213, 312 operation mode controlling unit
215 feature amount acquisition unit
216 first feature amount matching unit

What is claimed is:

1. An information processing device comprising:
a memory configured to store instructions; and
a processor configured to execute the instructions to:
acquire a result of biometric authentication based on acoustic characteristics obtained when a sound wave emitted from a wearable device toward a part of a head of a user passes through the part of the head of the user;
determine whether or not the user is wearing the wearable device; and
switch an operation mode among a plurality of operation modes including a first operation mode in which a process for determining whether the user is wearing the wearable device is executed and the biometric authentication is not executable, a second operation mode in which a process for the biometric authentication is executed, and a third operation mode in which a process for determining whether the user is wearing the wearable device and allowing the user to use the wearable device is executed, wherein, in a case where it is determined that the user is not wearing the wearable device in the third operation mode, the processor is further configured to execute the instructions to reset the result of the biometric authentication and switch the operation mode from the third operation mode.

2. The information processing device according to claim 1, wherein a power consumption in the second operation mode is greater than a power consumption in the first operation mode.

3. The information processing device according to claim 1, wherein an operation mode of the wearable device is switched from the first operation mode to the second operation mode in a case where it is determined that the user is wearing the device.

4. The information processing device according to claim 1,
wherein a power consumption in the third operation mode is greater than a power consumption in the second operation mode.

5. The information processing device according to claim 1, wherein an operation mode of the wearable device is switched from the second operation mode to the third operation mode in a case where the result of the biometric authentication indicates that the user is allowed to use the wearable.

6. The information processing device according to claim 1, wherein a matching of the acoustic characteristics for the biometric authentication is performed by the wearable device.

7. The information processing device according to claim 1, wherein a matching of the acoustic characteristics for the biometric authentication is performed by a device that is able to communicate with the wearable device.

8. The information processing device according to claim 1,
wherein the biometric authentication includes a first biometric authentication and a second biometric authentication having higher accuracy than the first biometric authentication,
wherein the second operation mode is a mode in which a process for the first biometric authentication is executable, and
wherein the plurality of operation modes further includes a fourth operation mode in which a process for the second biometric authentication is executable.

9. The information processing device according to claim 8, wherein a power consumption in the fourth operation mode is greater than a power consumption in the second operation mode.

10. The information processing device according to claim 8, wherein an operation mode of the wearable device is switched from the second operation mode to the fourth operation mode in a case where it is difficult to determine whether or not the user can use the wearable device by the first biometric authentication.

11. The information processing device according to claim 8,
wherein a matching of the acoustic characteristics for the first biometric authentication is performed by the wearable device, and
wherein a matching of the acoustic characteristics for the second biometric authentication is performed by a device that is able to communicate with the wearable device.

12. The information processing device according to claim 8,
wherein the third operation mode allows the user to use a function of the wearable device, and
wherein a power consumption in the third operation mode is greater than a power consumption in the fourth operation mode.

13. The information processing device according to claim 12, wherein an operation mode of the wearable device is switched from the second operation mode or the fourth operation mode to the third operation mode in a case where the first or second biometric authentication indicates that the user is allowed to use the wearable device.

14. The information processing device according to claim 1, wherein the biometric authentication is performed by matching acoustic characteristics of an ear canal.

15. The information processing device according to claim 1, wherein the wearable device is an acoustic device that is worn on an ear of the user.

16. The information processing device according to claim 1, wherein the wearable device is a wireless device that operates by receiving a power supply from a battery built in the wearable device.

17. A wearable device emitting a sound wave toward a part of a head of a user to perform a biometric authentication based on acoustic characteristics obtained when the sound wave passes through the part of the head of the user comprising:
a memory configured to store instructions; and
a processor configured to execute the instructions to:
perform the biometric authentication;
determine whether or not the user is wearing the wearable device; and
switch an operation mode among a plurality of operation modes including a first operation mode in which a process for determining whether the user is wearing the wearable device is executed and the biometric authentication is not executable, a second operation mode in which a process for the biometric authentication is executed, and a third operation mode in which a process for determining whether the user is wearing the wearable device and allowing the user to use the wearable device is executed,
wherein, in a case where it is determined that the user is not wearing the wearable device in the third operation mode, the processor is further configured to execute the instruction to reset the result of the biometric authentication and switch the operation mode from the third operation mode to the first operation mode.

18. An information processing method comprising:
acquiring a result of biometric authentication based on acoustic characteristics obtained when a sound wave emitted from a wearable device toward a part of a head of a user passes through the part of the head of the user;
determining whether or not the user is wearing the wearable device; and
switching, an operation mode among a plurality of operation modes including a first operation mode in which a process for determining whether the user is wearing the wearable device is executed and the biometric authentication is not executable, a second operation mode in which a process for the biometric authentication is executed, and a third operation mode in which a process determining whether the user is wearing the wearable device and allowing the user to use the wearable device is executed, wherein, in a case where it is determined that the user is not wearing the wearable device in the third operation mode, the switching includes resetting the result of the biometric authentication and switching the operation mode from the third operation mode to the first operation mode.

19. A non-transitory storage medium storing a program that causes a computer to perform:

acquiring a result of a biometric authentication based on acoustic characteristics obtained when a sound wave emitted from a wearable device toward a part of a head of a user passes through the part of the head of the user;

determining whether or not the user is wearing the wearable device; and switching an operation mode among a plurality of operation modes including a first operation mode in which a process for determining whether the user is wearing the wearable device is executed and the biometric authentication is not executable, a second operation mode in which a process for the biometric authentication is executed, and a third operation mode in which a process for determining whether the user is wearing the wearable device and allowing the user to use the wearable device is executed, wherein, in a case where it is determined that the user is not wearing the wearable device in the third operation mode, the switching includes resetting the result of the biometric authentication and switching the operation mode from the third operation mode to the first operation mode.

* * * * *